(12) United States Patent
Cummings et al.

(10) Patent No.: US 6,432,416 B1
(45) Date of Patent: *Aug. 13, 2002

(54) ANTI-MICROBIAL POWER COATING

(75) Inventors: Frederick L. Cummings, Richmond, TX (US); Peter Gottschling, Columbus, OH (US); Jeffrey R. Hagerlin, Houston, TX (US); Owen H. Decker, Spring, TX (US); M. Aaron Sparks, Houston, TX (US)

(73) Assignee: Dupont Powder Coatings USA, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/713,882

(22) Filed: Nov. 16, 2000

Related U.S. Application Data

(63) Continuation-in-part of application No. 09/624,155, filed on Jul. 24, 2000, which is a continuation of application No. 09/165,839, filed on Oct. 2, 1998, now Pat. No. 6,093,407.
(60) Provisional application No. 60/061,099, filed on Oct. 3, 1997.

(51) Int. Cl.[7] .............................. A61K 9/00; A61K 9/14; A61K 33/24; A61K 33/38; A61K 33/34
(52) U.S. Cl. ..................... 424/400; 424/405; 424/489; 424/617; 424/618; 424/630; 424/641; 514/951
(58) Field of Search ................................ 424/400, 405, 424/489, 617, 618, 630, 641; 514/951

(56) References Cited

U.S. PATENT DOCUMENTS

| | | | | |
|---|---|---|---|---|
| 4,755,585 | A | | 7/1988 | Hanson et al. ............... 528/182 |
| 4,906,464 | A | | 3/1990 | Yamamoto et al. ............ 424/78 |
| 4,938,955 | A | | 7/1990 | Niira et al. .................... 424/79 |
| 6,093,407 | A | * | 7/2000 | Cummings et al. .......... 424/400 |
| 6,123,925 | A | | 9/2000 | Barry et al. ................... 424/49 |

FOREIGN PATENT DOCUMENTS

| | | | |
|---|---|---|---|
| JP | 08060036 | * | 5/1996 |

OTHER PUBLICATIONS

Healthshield™ Antimicrobial, AgION Technologies LLC, printed from http://healthshield.com, 2000.

* cited by examiner

*Primary Examiner*—Kevin E. Weddington
(74) *Attorney, Agent, or Firm*—Trop, Pruner & Hu, P.C.

(57) ABSTRACT

Improved powder coatings exhibit enhanced resistance to bacterial and fungal attack, while possessing excellent toughness, appearance, corrosion resistance, durability, processability, and ease of application. The coating is comprised of anti-microbial agents melt-processed into the matrices of coating powders or bonded to coating powders. An article may be coated with a thermoset or thermoplastic powder that may be applied by electrostatic spray or fluidized bed or by thermal or flame spray.

16 Claims, 1 Drawing Sheet

ANTI-MICROBIAL POWER COATING

This application a continuation-in-part of application Ser. No. 09/624,155 filed on Jul. 24, 2000, which is a continuation of application Ser. No. 09/165,839 filed on Oct. 2, 1998 that was issued as U.S. Pat. No. 6,093,407 on Jul. 25, 2000, that was based on provisional application Serial No. 60/061,099, filed on Oct. 3, 1997.

BACKGROUND

This invention relates generally to powder coatings and particularly to anti-microbial powder coatings.

Public concern about the health hazards arising from microorganisms such as bacteria, fungi, viruses and the like is high. Many people are concerned that contact with objects in public facilities may result in illness. Also, it is desirable to prevent biological defacement of object surfaces due to the growth of microorganisms.

Thus, a number of efforts have been undertaken to produce objects with the ability to kill or inhibit the growth or reproduction of microorganisms, which is termed "anti-microbial activity" herein. For example, plastic materials with anti-microbial activity are known. The resulting plastic products then exhibit some degree of anti-microbial activity.

For example, some toys for young children include anti-microbial agents (i.e., agents with anti-microbial activity) within a plastic matrix. These anti-microbial agents, which are believed to be safe, are believed to inhibit the growth of various microorganisms. Anti-microbial agents in the final coatings including paint and powder coatings are known. However, none of the existing techniques in powder coatings have gained substantial acceptance.

Therefore, there is a continuing need for improved coatings and particularly for improved powder coatings that exhibit anti-microbial activity when applied to substrates.

SUMMARY

An anti-microbial powder coating composition includes an anti-microbial agent homogeneously dispersed within particles of a resin-based powder.

DETAILED DESCRIPTION

Figure 1:
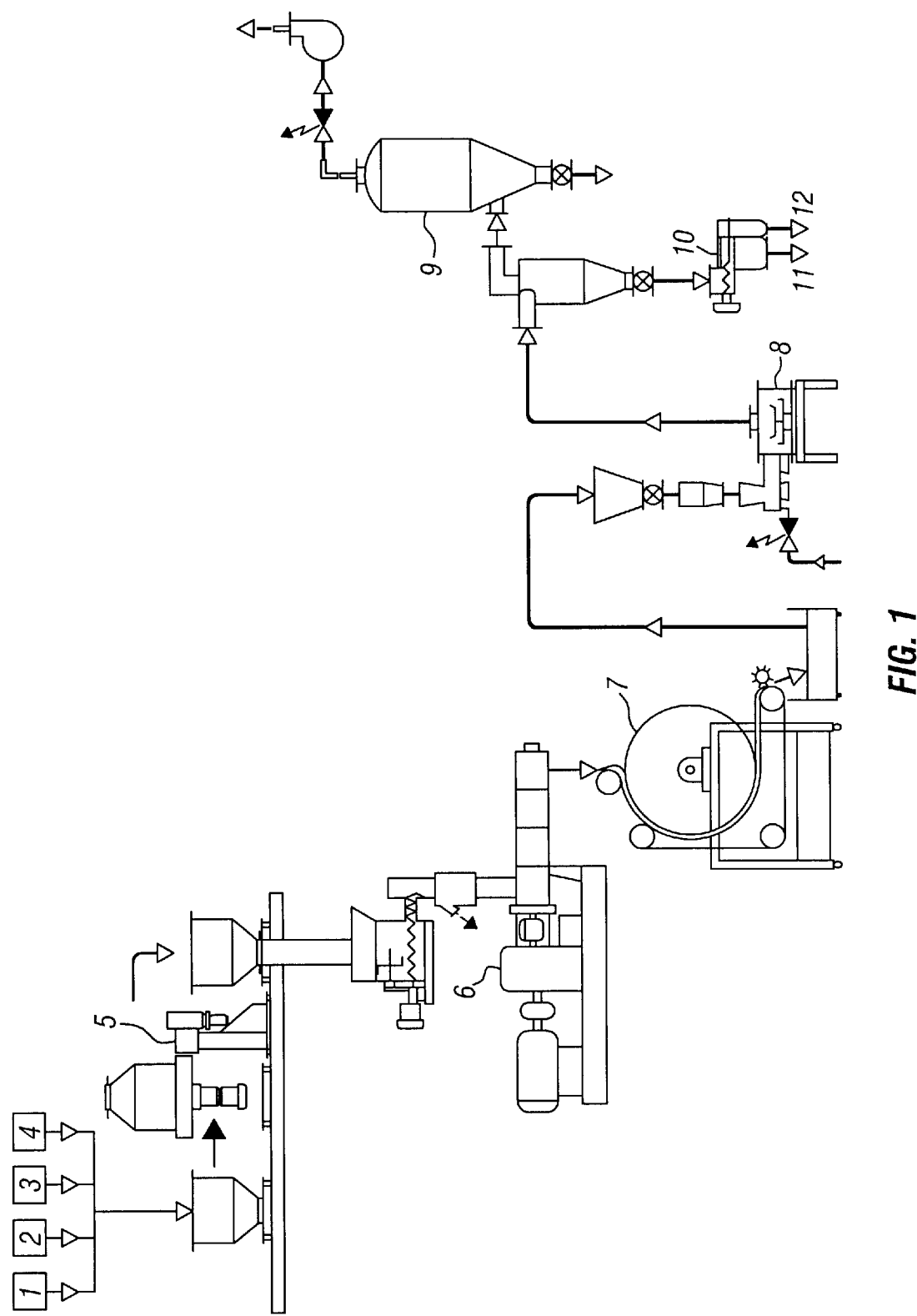
FIG. 1 is a diagrammatic depiction of a process for making a powder coating.

A stable anti-microbial powder coating composition may coat a product that may be exposed to bacteria and fungal spores. The powder coating may be made by a process that produces a homogeneous distribution of anti-microbial agents that may promote consistent and efficient anti-microbial activity. Once coated with the anti-microbial powder coating, a substrate may be protected from physical abuse by the film's physical properties and durability and from degradation due to attack by microorganisms and also potentially protecting the user from various microorganisms.

The powder coating formulation may be applied to the substrate so that bacterial or fungal contact with the coating either kills them or at least inhibits their growth. For example, in some embodiments, anti-microbial activity with respect to *Staphylococcus aureus, Escherichia coli, Bacillus subtillus, Streptococcus faecalis, Salmonella typhinurium, Pseudomonas aeruginosa*, and other Gram positive and Gram negative bacteria may be achieved. Powder coating formulations, in some embodiments, may also inhibit the growth of certain higher organisms like algae, fungi, filamentous fungi (Aspergillus, Aureobasidium, Botrytis, Ceratostomella, Cuvularia, Fusarium and Penicillium species), yeast and also, some viruses.

Potential applications for these improved powder coatings may include, for example, food preparation areas, restrooms, hospitals, garbage disposals, stockyard areas, animal feed troughs, schools, kitchens, swimming pool areas, dishwashers, automobile fixtures, public access fixtures, public seating, public transportation fixtures, toys, and other industrial, agricultural, commercial or consumer products.

The resin may be one or more of the thermosetting and/or thermoplastic resins including those based on epoxy, polyester, acrylate, acrylic, polysiloxane and/or polyurethane resins. The coating may also include from about 0.1 percent to about 10 percent by weight of the total composition of one or more liquid or solid anti-microbial agents.

Examples of thermoplastic or thermosetting coatings that may be used, include: but are not limited to epoxies, saturated and unsaturated polyesters, carboxylic acid-functional polyesters, hydroxyl-functional polyesters, epoxy/polyester hybrids, acrylics, epoxy/acrylic hybrids, glycidyl-functional acrylics, polyester-urethanes, acrylic urethanes and siloxanes. Thermoplastic powder coatings that may be useful include, but are not limited to nylon, polyvinyl chloride (PVC), polyethylene, polyethylene terephthalate (PET), polybutylene terephthalate (PBT), and polypropylene as examples. These powder coatings may be cured or fused by thermal or photochemical methods.

The anti-microbial agents include but are not limited to phthalimides, acetamides, phthalonitriles, hydroxy benzoates, isothiazolinones, nitropropane diols, carbamates, methyl ureas, benzimidazoles, salicylanilides, mercury acetates, organozinc compounds, metals such as silver, copper and zinc, and ions of such metals.

Among the liquid anti-microbial agents which are suitable in certain applications, a preferred anti-microbial agent is dibromocyanoacetamide (for example, Amerstat® 300 made by Drew Industrial Division of Ashland Chemicals, Boonton, N.J. 07005).

In addition, solid anti-microbial agents that are preferred include 2-bromo-2-nitropropane-1,3-diol (for example, Canguard® 409 made by Angus Chemical Co., Buffalo Grove, Ill. 60089) and 3,5-dimethyltetrahydro-1,3,5-2H-thiazine-2-thione (for example, Nuosept® S made by Creanova, Inc., Piscataway, N.J. 08855 or Troysan® 142 made by Troy Chemical Corp., West Hanover, N.J. 07936).

Other solid anti-microbial agents include N-(trichloromethyl)-thiophthalimide (for example, Fungitrol® 11 made by Creanova, Inc.), butyl-p-hydroxy-benzoate (for example, Butyl Parabens® made by International Sourcing Inc., Upper Saddle River, N.J. 07458), diiodomethyl-p-tolysulfone (for example, Amical® WP made by Angus Chemical Co.), and tetrachloroisophthalonitrile (for example, Nuocide® 960 made by Creanova, Inc.).

Metals such as silver, copper and zinc and ions of such metals also have anti-microbial properties. Silver ions have widespread effect as an anti-microbial agent. For example, silver ions may be effective against bacteria such as *Escherichia coli* and *Salmonella typhimurium*, and mold such as *Asperigillus niger.*

Sources of silver for anti-microbial use include metallic silver, silver salts and organic compounds that contain silver. Silver salts may include for example: silver carbonate, silver sulfate, silver nitrate, silver acetate, silver benzoate, silver chloride, silver fluoride, silver iodate, silver iodide, silver lactate, silver nitrate, silver oxide and silver phosphates. Organic compounds containing silver may include for example, silver acetylacetonate, silver neodecanoate and silver ethylenediaminetetraacetate in all its various salts.

Silver containing zeolites (for example, AJ10D containing 2.5% silver as Ag(I), made by AgION™ Tech. L.L.C., Wakefield, Mass. 01880) are of particular use. Zeolites are useful because when carried in a polymer matrix they may provide silver ions at a rate and concentration that is effective at killing and inhibiting microorganisms without harming higher organisms.

The powder coating may be sprayed electrostatically onto a metal or nonmetal substrate. Charged particles of the powder coating are sprayed onto the substrate until a desired thickness is achieved. Other methods, such as fluidized bed coating methods, thermal spraying and flame spraying may also be used.

After the deposition is complete, the coated substrate is heated. For example, an electrical or gas fired oven may be used to cure or fuse the coating at temperatures in the range of 80° C. to 270° C. The curing time may be about five to twenty minutes for most substrates, but may vary from less than a minute to greater than one hour depending on the type of coating, the substrate, and the curing system. In addition to thermal methods, curing may also be achieved by electron beam or photochemical methods such as ultraviolet, infrared and the like. Curing of the coating can be effected by heat conduction, convection, radiation, or any combination of the three.

Advantageously, visible bubbling in the coating film after the curing process should be avoided. The presence of bubbles may indicate that some of the biocide may have been volatilized during the curing process. Advantageous anti-microbial agents should not produce visible bubbles indicative of volatilizing of the active element.

The powder coatings may be made by a melt extrusion method, as illustrated in FIG. 1. For example, a powder formulation includes more than one ingredient as represented by items 1–4. Fillers, extenders, flow additives, catalysts, hardeners, catalysts, pigments and other additives may be blended together with the resin and the anti-microbial agent in a premixer 5. The mixture may then be fed into an extruder 6 and heated to a temperature high enough to melt and mix the constituents. A temperature in the range of 50° C. to 150° C. may be sufficient. The molten extrudate may be immediately cooled by chill rolls 7 to form solid sheets.

The solid sheets may be further broken down to suitably sized chips. These chips are then fed into a grinder 8 which reduces the chips to fine particles. For example, particles having a mean particle size of about 10 microns to 180 microns are satisfactory. The resulting powder advantageously has a glass transition temperature that is greater than the storage temperature. A dust filter 9, a sieve screen 10, and powder inspection station 11 and 12 may also be provided.

The anti-microbial agents are uniformly dispersed in the resin formulation (including the curing agent) during the premix stage. This is advantageous because there is no requirement that the anti-microbial agents have a specific particle size or particle size distribution. The anti-microbial agents are chosen to survive the extrusion process and the subsequent curing process in sufficient concentration to exhibit an anti-microbial effect in the final coating. In addition, it is preferable that the anti-microbial agent does not adversely change any important property of the final coating such as color.

Solid anti-microbial agents including those, which are metallic or metal containing, may be premixed directly with the formulation components. Alternatively, the particles of anti-microbial agent may be bonded with pre-formed powder coating particles using impact fusion. This process is also known in the art as "fusion bonding." With either method, mixing the anti-microbial particles with coating particles of the same particle size distribution is not necessary.

Liquid anti-microbial agents can be mixed readily with other components in the premix prior to extrusion. Liquid anti-microbial agents often are difficult to dry blend into a powder to a concentration that consistently, effectively protects against bacteria or fungi. Alternatively, liquid anti-microbial agents may be mixed initially with particles of a solid support material such as a silica, clay or other resins in a masterbatch. The dry mixture containing the liquid anti-microbial agent may then be mixed into a formulation of resin.

For example, the liquid anti-microbial agent may be mixed at room temperature using high shear into fumed silica yielding high concentrations of active ingredients. The resulting granular solid may then be treated as a solid anti-microbial agent. For example, concentrations of approximately 66 percent of active ingredients in fumed silica may be utilized.

Liquid and solid anti-microbial agents also may be incorporated within the powder coating particle by dissolving or mixing them and the other powder coating formulation components in a suitable solvent, e.g., organic liquids or supercritical fluids, and then removing the liquid in such a manner as to yield a powder or a solid product which can be processed into a powder.

A suitable powder coating material, which is utilized in examples one through four is Gold Bond III, a catalyzed epoxy powder coating sold by DuPont Powder Coatings, Inc., of Houston, Tex. Fillers and extenders, melt flow additives, dry flow additives, pigments and other additives may also be used to enhance specific physical properties, aesthetics, durability or other attributes.

Other powder coating materials, utilized in example 5, include urethane-cured polyesters compositions and triglycidylisocyanurate (TGIC) epoxy-cured polyesters compositions. Fillers, flow aids, degassing aids and pigments may also be used to enhance certain properties of the powder coating such at aesthetics and durability.

EXAMPLE 1

A long-term anti-microbial activity test was carried out to determine if selected anti-microbial agents maintain their anti-microbial activity after being incorporated into powder coatings and cured.

Six anti-microbial agents were selected for experimentation. They are Fungitrol® 11, Amerstat® 300, Nuocide® 960, Nuosept® S, Propyl Parabens®, and Butyl Parabens®. For each powder coating formulation, one of the six anti-microbial agents was added at concentrations of 0.1 percent and 1 percent of the total resin weight.

Samples containing one of the six additives at the two concentrations in the coating matrix were prepared. The samples are coated on 2.54 cm. by 2.54 cm. by 0.08 cm. steel coupons. Both the front and the back of the coupons were coated with a given coating formulation. The edges were coated with a black silicone resin to prevent rusting of the coupon, which might interfere with the interpretation of the experimental results. Controls containing the coating formulation with no additive and controls containing only the black silicone resin used for edge coverage were included.

The target bacterial organisms were *Pseudomonas aeruginosa, Escherichia coli*, and *Salmonella typhinurium*. Five groups of samples were prepared. For each of the six additives, two panels with a coating thickness of 7 to 8 mils were cured with a normal schedule of 193° C. for 10 minutes. For each of the six additives, two panels with anti-microbial agent concentrations of 0.1 percent and 1 percent and with a coating thickness of 7 to 8 mils were cured with a normal schedule. Each of the following samples was prepared with an additive concentration of 1 percent of the resin by weight. For each of the six additives, two panels were prepared with a coating thickness of 3 to 4.5 mils and cured with a normal schedule.

The results were then rated on a scale of "0" (good performance) to "4" (poor performance) based on the number of colony-forming units observed. The growth ratings, which were averaged over the different samples, are based on the following numerical rating system:

0=No contamination (sterile).
1=Trace of contamination (1–9 colonies per "streak-inch").
2=Light contamination (10–99 colonies per "streak-inch").
3=Moderate contamination (greater than 100 colonies, but still distinguishable).
4=Heavy contamination (continuous smear of growth).

Resistance to fungal growth was tested generally in accordance with ASTM D5590-95. The organisms targeted were *Aspergillus niger* (ATCC 6275), *Penicillium funiculosum* (ATCC 11797), and *Aureobasidium pullulans* (ATCC 9348) in a mixed spore suspension. Samples were aseptically placed onto a modified malt agar plate and then each sample was inoculated. The following data was determined after four weeks:

| ADDITIVE | AVERAGE BACTERIAL COVERAGE |
| --- | --- |
| CONTROLS | 3.0 ± 1.7 |
| FUNGITROL ® 11 | 2.8 ± 1.8 |
| PROPYL PARABENS ® | 3.7 ± 0.5 |
| BUTYL PARABENS ® | 2.6 ± 1.3 |
| AMERSTAT ® 300 | 1.6 ± 1.5 |
| NUOCIDE ® 960 | 3.0 ± 1.3 |
| NUOSEPT ® S | 3.6 ± 0.5 |

The Amerstat® 300 showed significantly improved bacterial coverage compared to the other additives and the control. The effect of decreasing the additive concentration was minimal. Decreasing the coating thickness had very little effect on the anti-microbial activity of the coating.

Among the tested additives, Propyl Parabens® and Nuosept® S did not appear to improve the activity relative to the control and thus it was concluded that little or no effect on the long-term anti-microbial properties given the chosen resin matrix.

The same samples were also exposed to fungus spores for a period of four weeks. Results of the study showed that several of the coatings showed no growth of fungi on their surface after four weeks of exposure. At a concentration of 1 percent, powder coatings made with the Butyl and Propyl Parabens®, and Nuocide® 960 were free of visible fungal growth. Fungitrol® 11 and Amerstat® 300 had a very small amount of fungal growth. The Nuosept® S did not show conclusive fungal resistance.

An additional study was then undertaken using AATCC Test Method 30-1993, Part III. In this test, a control, Fungitrol®11, Amerstat® 300, Nuocide® 960, Nuosept® S, Propyl Parabens® and Butyl Parabens® formulations were applied to steel coupons, as described previously. The samples were placed in sterile Petri dishes with Seboraud Dextrose Agar, inoculated with *Aspergillus niger*, (AATCC 6275), and incubated at 28° C. for three weeks. The fungus was placed on top of the coating as well as on the agar.

At the end of the three-week test period, only the control showed biological activity. When examined visibly and by microscope at one, two and three weeks, the control showed visible macroscopic fungal growth on its surface. The other formulations' surfaces did not have macroscopic or microscopic growth. Macroscopic growth was visible on the agar surfaces. However, it stopped at the coating edge. Since no zones of inhibition in the agar were visible, the anti-microbial agent is believed not to have leached out during exposure.

EXAMPLE 2

In order to determine how fast the anti-microbial agents are able to work, shorter-term tests were also conducted. In many applications, it is desirable that the anti-microbial agent operates quickly.

Steel coupons were coated with the Fungitrol® 11, Butyl Parabens®, and Amerstat® 300 anti-microbial formulations, at 0.1 percent and 1 percent, and exposed as per ASTM D 5588-94 to a mixture containing the bacteria *Pseudomonas aeruginosa*, *Staphylococcus aureus*, and *Escherichia coli*. After the coupons were washed with a 70 percent ethanol/water solution, they were placed in a sterile Petri dish, inoculated, and incubated at 32° C. for the duration of the test.

At appropriate intervals, each sample was checked for the presence of viable microorganisms by streaking each sample with a sterile cotton swab, then streaking the swab onto Tryptic Soy Agar. The plates were incubated for 48 hours at 32° C. The absence of microbial growth along the streak indicated that the corresponding sample did not contain viable microbial cells. The presence of microbial growth would indicate non-sterility, i.e., the sample contained viable microbial contamination.

The samples were examined for low levels of bacterial contamination by transferring an aliquot with a sterile cotton swab to a Tryptic Soy Broth in culture tubes. The tubes were incubated for 24 hours at 32° C., streaked onto Tryptic Soy Agar plates and the plates were incubated for 24 to 48 hours at 32° C.

Heavy bacterial growth was detected initially and after 4 hours for all samples, however, after 24 hours of exposure, differentiation in growth was visible among the samples. After 72 hours of incubation, the Butyl Parabens®-coated samples were free of bacterial growth and were actually sterile. The control showed low to heavy growth. The Amerstat® 300 and Fungitrol® 11 did not show conclusive results.

Next, steel coupons were coated with the anti-microbial formulations listed above and exposed per ASTM D 5588-94 to a mixture containing the fungus spores of *Aspergillus niger*, *Penicillium funiculosum*, and *Aerobasidium pullulans*. After the coupons were washed with a 70 percent ethanol/water solution, they were placed in a sterile Petri dish, inoculated, and incubated at 28° C. for the duration of the test. At appropriate intervals, each sample was checked for the presence of viable microorganisms by streaking each sample with a sterile cotton swab, then streaking the swab onto Potato Dextrose Agar (adjusted to pH 3.5 for fungi). These plates were also incubated at 28° C.

The absence of microbial growth along the streak indicated that the corresponding sample did not contain viable microbial cells. The presence of microbial growth would indicate non-sterility, i.e., the sample contained viable microbial contamination.

Heavy fungal growth was detected initially and after 4 hours for all samples. However, once again, at 24 hours of exposure, differentiation among the samples was observed. After 72 hours of incubation, Fungitrol® 11- and Butyl Parabens®-coated samples were free of (or showed very low levels of) bacterial growth.

EXAMPLE 3

Using AATCC Test Method 147 (Nutrient Broth, incubated at 37° C. for 18 to 24 hours), another test of very short term efficacy was undertaken. Cured powder coating formulations containing (0.1 percent and 1 percent) Fungitrol® 11, Amerstat® 300, Nuocide® 960, Nuosept® S, Propyl Parabens®, and Butyl Parabens® were exposed to a concentration of (inoculated) *Staphylococcus aureus, Escherichia coli*, and *Salmonella choleraesuis* for an exposure period of 18 to 24 hours. None of the formulations were effective in significantly killing the microorganisms over the short test cycle.

EXAMPLE 4

The next experiments were conducted, according to the procedure of Example 3, to evaluate the effect of higher anti-microbial concentration on short-term anti-microbial activity. Coating powders containing 2 percent Amerstat® 300, 4 percent Troysan® 174P, 5 percent Canguard® 409, 3 percent Irgasan® DP 400, 5 percent Amical® WP, 5 percent Nuosept® S, 10 percent Nuosept® S, 5 percent Nuocide® PCMC, and 10 percent Nuocide® PCMC were used in the next experiment.

Each formulation was loaded with anti-microbial agent until the powder became unstable. For example, if the powder sintered or cured too quickly, the concentration was reduced.

Significant zones of inhibition were achieved by the powder coatings containing 5 percent Canguard® 409, (bronopol), 3 percent Irgasan® DP 400 (triclosan, 5-chloro-2-(2,4-dichloro-phenoxy)phenol) and 5 percent and 10 percent Nuosept® S. The bronopol (2-bromo-2-nitropropane-1,3-diol) formulation performed better than the triclosan formulation in inhibiting the growth of *Escherichia coli* and *Salmonella choleraesuis*.

The Nuosept® S performed as well as or better than the triclosan formulation in inhibiting the growth of *Escherichia coli* and *Salmonella choleraesuis*.

Thus, one preferred anti-microbial composition includes a mixture of anti-microbial agents that have short-term efficacy with agents having long-term efficacy. One preferred mixture includes 5 percent Nuosept® S and 0.1 percent Amerstat® 300 in a powder coating formulation.

EXAMPLE 5

Experiments were performed to determine the concentration and anti-microbial effects of silver when a silver zeolite is incorporated into a powder coating composition. Silver zeolite was obtained from AgION™ Technologies, L.L.C., Wakefield Mass. 01880. The zeolite was homogeneously distributed into powder coating mixtures during the premix as described previously. The resultant compositions were then melt-extruded, solidified between chilled rolls, broken up and ground into a powder. The powders were scalped to remove particles larger than 180 microns.

Two types of powder coatings were prepared for these experiments. One powder coating type was a urethane-cured hydroxyl-functional polyester coating containing 100 parts of a hydroxyl resin (Ruco 102 HYD made by Ruco Polymer Corp., Hicksville, N.Y. 11801) and either 22.1 parts of a caprolactam-blocked isocyanate curing agent (Alcure 4400 made by McWhorter Tech. Inc., Ennis, Tex. 75119) or 27.7 parts of a uretidione-blocked isocyanate curing agent (Alcure 4147 made by McWhorter Tech. Inc.). See Table 1.

The other powder coating type was a triglycidylisocyanurate (TGIC)-cured carboxyl-functional polyester coating containing 100 parts of a carboxyl polyester resin (Uralac P-2400 made by DSM Resins US Inc., Augusta, Ga. 30903) and 7.5 parts of a TGIC curing agent (Araldite PT-810 made by Vantico Inc., Los Angeles, Calif. 90023). See Table 2.

Flow aids, fillers, degassing aids and pigments were also utilized in both types of powder coating compositions as indicated in Tables 1 and 2.

In the urethane-cured polyester composition, the silver zeolite AJ10D, containing 2.5% silver as Ag (I), was added so that its final concentration was one or three percent by weight of the total composition, as indicated in Table 1. In the TGIC-cured polyester composition, the same silver zeolite was added so that its final concentration was one, four or ten percent by weight of the total composition, as indicated in Table 2.

Both types of powder coating compositions were applied to grounded aluminum panels that were 0.020 inches thick. The powder coating thickness was from 1.8 to 2.5 mils. The powder coated panels were baked for 10 minutes at 400° F. and then evaluated for the concentration of silver in the coating, the concentration of surface silver and anti-microbial activity of the coating.

The total concentration of silver for each aluminum panel was determined by taking a percentage of the amount of silver contained in the zeolite and the amount of zeolite added to each powder coating compositions. For example, the AJ210D zeolite has 2.5% Ag. If the zeolite made up 1% of the total powder coating composition, then the total concentration of silver in the composition would be 0.025%.

To determine surface silver concentration, the aluminum panels were trimmed to 2 inches by 2 inches and soaked for 24 hours in 25 ml. of 0.8M $NaNO_3$ solution. Aliquots of the solution were taken and tested for the concentration of silver ion by Graphite Furnace Atomic Absorption.

To determine silver's anti-microbial activity, 2 inch by 2 inch coated aluminum panels were inoculated with suspensions of *Escherichia coli* and incubated at 37° C. for 24 hours. The panels were then rinsed and the rinsate was serially diluted. The serial dilutions were applied to agar medium and further incubated to determine the percentage of bacterial growth.

Referring to Table 1, aluminum test panels coated with urethane-cured polyester compositions contained 0, 1, or 3 percent of the total powder coating composition of silver zeolite, as shown in test panels 1 through 6. All panels were based on a hydroxyl polyester resin. Panels 1 through 5 were cured with a caprolactam-blocked isocyanate curing agent. Panel 6 was cured with a uretidione internally-blocked isocyanate curing agent. Panels 4 and 5 also contained pigment and filler. Flow aids and degassing aids were also present in the powder coating composition.

Still referring to Table 1, test panel 1, a control panel, had 0% silver zeolite, no silver in the coated panel and no detectable surface silver. Test panel 2 with it 1% silver zeolite had 0.025% silver in the coating, 8.2 mg/L of which was surface silver. Test panels 3 through 6 all had 3% silver zeolite, therefore 0.075% silver in the powdered coating. However, the surface silver concentrations were variable for these panels with panels 3, 4, 5 and 6 having 8.1, 8.6, 4.5, and 15 mg/L surface silver respectively.

Regardless of the concentration of surface silver, none of the test panels powder coated with a urethane-cured polyester composition supported bacterial growth as indicated in Table 1. However, the control aluminum panel, panel 1 of Table 1, lacking silver zeolite hence lacking silver, did support bacterial growth. Thus, in urethane-cured polyester powder coating compositions silver zeolite is an effective carrier to supply anti-microbial silver in the powder coating.

TABLE 1

Urethane-Cured Polyester Compositions

| Components | Test Panels | | | | | |
|---|---|---|---|---|---|---|
| | 1 | 2 | 3 | 4 | 5 | 6 |
| Hydroxyl Polyester Resin (parts) Ruco 102 HYD from Ruco Polymer Corp. Hicksville, NY 11801 | 100 | 100 | 100 | 100 | 100 | 100 |
| Caprolactam-Blocked Isocyanate Curing Agent (parts) Alcure 4400 from McWhorter Tech. Inc., Ennis, TX 75119 | 22.1 | 22.1 | 22.1 | 22.1 | 22.1 | — |
| Uretidione-Blocked Isocyanate Curing Agent (parts) Alcure 4147 from McWhorter Tech. Inc. | — | — | — | — | — | 27.7 |
| Flow Aid (parts) L-7605 Silwet Flow Aid from OSI Specialties | 0.62 | 0.62 | 0.62 | 0.62 | 0.62 | 0.62 |
| Degassing Aid (Parts) Benzoin Degassing Aid from Estron Chem. Inc., Calvert City, KY 42029 | 0.60 | 0.60 | 0.60 | 0.60 | 0.60 | 0.60 |
| Carbon Black Pigment (parts) Raven 1200 Carbon Black Pigment from Columbian Chemicals Pigment Co., Marietta, GA 30062 | — | — | — | 1.33 | — | — |
| $TiO_2$ Pigment (parts) R-960 from Dupont | — | — | — | — | 55.6 | — |
| Filler (parts) Sparwhite $BaSO_4$ Filler from Mountain Minerals, Calgary, Alberta, Canada T2P 2Z2 | — | — | — | 13 | 13 | — |
| Silver Zeolite (%, based on the sum of the other components) AJ10D Antimicrobial from AgION Tech. L.L.C., Wakefield, MA 01880 | — | 1 | 3 | 3 | 3 | 3 |
| Silver Concentration in Coating (%) | 0.0 | 0.025 | 0.075 | 0.075 | 0.075 | 0.075 |
| Surface Silver (mg/L) | 0.0 | 8.2 | 8.1 | 8.6 | 4.5 | 15 |
| Bacteriostatic Activity (Kill Efficiency, %) | 0.0 | 99.99 | 99.99 | 99.99 | 99.99 | 99.99 |

Referring to Table 2, aluminum test panels were coated with a carboxyl polyester resin based powder coating composition that was cured with a TGIC curing agent. Test panels 7, 8, 9 and 10 contained 0, 1, 4 and 10 percent silver zeolite, respectively. For test panels 7 through 10, coating compositions also contained a flow aid, a degassing aid, a pigment and a filler.

Test panel 7, shown in Table 2, did not contain silver zeolite in the powder coating composition, thus, there was no silver in the powder coating and no detectable surface silver. Silver zeolite was added to the coating compositions of test panels 8, 9 and 10 giving the powder coated substrates silver concentrations of 0.025%, 0.1% and 0.25% respectively. Detectable surface silver for test panels 8, 9 and 10 were 1.9, 14.8 and 34.4 mg/L respectively.

Unlike the urethane-cured polyester coated panels, the TGIC epoxy-cured polyester coated test panels only showed anti-microbial activity at the highest concentration of zeolite used. That is, test panel 10 showed a 98.6% inhibition of bacterial growth as compared to a zeolite-free control whereas test panels 8 and 9 did not exhibit any inhibition of bacterial growth. Thus, in TGIC epoxy-cured polyester powder coating compositions, a higher percentage of silver zeolite may be needed to provide surface silver ions in a concentration that is effective as an anti-microbial agent.

TABLE 2

TGIC Epoxy-Cured Polyester Composition

| Component | Test Panels | | | |
|---|---|---|---|---|
| | 7 | 8 | 9 | 10 |
| Carboxyl Polyester Resin (parts) Uralac P-2400 from DSM Resins U.S., Inc. Augusta, GA 30903 | 100 | 100 | 100 | 100 |
| TGIC Curing Agent (parts) Araldite PT-810 from Vantico Inc., Los Angeles, CA 90023 | 7.5 | 7.5 | 7.5 | 7.5 |
| Flow Aid (parts) Modaflow III Flow Aid From Estron Chem. Inc., Calvert City, KY 42029 | 1.3 | 1.3 | 1.3 | 1.3 |
| Degassing Aid (parts) Benzoin Degassing Aid from Estron Chem. Inc. | 1.2 | 1.2 | 1.2 | 1.2 |
| Pigment (parts) R-960 $TiO_2$ Pigment from Dupont | 63 | 63 | 63 | 63 |
| Filler (parts) Sparwhite $BaSO_4$ Filler from Mountain Minerals, Calgary, Alberta, Canada T2P 2Z2 | 14 | 14 | 14 | 14 |
| Silver Zeolite (%, based on the sum of the other components) AJ10D Antimicrobial from AgION Tech. L.L.C., Wakefield, MA 01880 | 0 | 1 | 4 | 10 |
| Silver Concentration in Coating (%) | 0.0 | 0.025 | 0.10 | 0.25 |

TABLE 2-continued

TGIC Epoxy-Cured Polyester Composition

| | Test Panels | | | |
|---|---|---|---|---|
| Component | 7 | 8 | 9 | 10 |
| Surface Silver (mg/L) | 0.0 | 1.9 | 14.8 | 34.4 |
| Bacteriostatic Activity (Kill Efficiency, %) | 0.0 | 0.0 | 0.0 | 98.6 |

In sum, both types of powder coating compositions containing a silver zeolite showed anti-microbial activity. However, the urethane-cured powdered coating composition had superior anti-microbial activity.

EXAMPLE 6

This example illustrates the "bonding" process of heating and impact fusion that may be used to produce homogenous dispersions of antimicrobial agents on powder coatings. To 5.0 lbs. of the coating powder of Test Panel 2 from Example 5 above, is added 0.0505 lbs. of AgION AJ10D antimicrobial zeolite, to yield a mixture containing 1% AJ10D zeolite. The mixture is then blended at 3000 rpm in a 10-liter capacity Papenmeier TGHK-10 High Intensity Mixer (Merlin Process Equipment, Inc., Houston, Tex.), during which time its temperature rises to between 50 and 60° C. Blending time is adjusted so that at the end of the process the temperature of the powder is approximately equivalent to its glass transition temperature. This process homogeneously disperses the AJ10D and substantially impact fuses (or "bonds," or "fusion bonds")it to the powder coating particles.

What is claimed is:

1. An anti-microbial powder coating composition comprising one or more anti-microbial metals or metal ions homogeneously dispersed within particles of a resin-based powder.

2. The composition of claim 1 wherein the anti-microbial metal or metal ion is silver.

3. The composition of claim 2 wherein the silver is in the form of a silver ion carried by a zeolite.

4. The composition of claim 2 wherein the silver is supplied by a silver salt.

5. The composition of claim 2 wherein the silver is supplied by an organic compound containing silver.

6. The composition of claim 2 wherein the powder coating composition comprises a thermosetting composition based on a cured polyester resin composition.

7. The composition of claim 6 wherein the silver is carried by a zeolite.

8. The composition of claim 7 wherein the polyester resin composition is cured with a urethane curing agent.

9. The composition of claim 8 wherein the urethane curing agent is a caprolactam-blocked isocyanate.

10. The composition of claim 8 wherein the urethane curing agent is a uretidione-blocked isocyanate.

11. The composition of claim 8 wherein the silver containing zeolite is about 1 to 3 percent of the sum of the components comprising the powder coating composition.

12. The composition of claim 7 wherein the polyester resin composition is cured with a triglycidylisocyanurate.

13. The composition of claim 12 wherein the silver containing zeolite is about 10 percent of the sum of the components comprising the powder coating composition.

14. A method for preparing an anti-microbial powder coating composition comprising homogeneously mixing an anti-microbial metal or metal salt into a powder coating pre-mix.

15. The method of claim 14, further comprising blending the components of the powder coating composition using a premixer, feeding the mixture into an extruder, and heating the mixture to a temperature high enough to melt it, cooling the melt, and processing the solid extrudate into a coating powder.

16. The method of claim 15 further comprising treating the powder coating particles by impacting the powder coating particles with particles containing an anti-microbial metal or metal salt to adhere the anti-microbial metal or metal salt to the coating powder particles.

* * * * *